US00PP31398P2

(12) United States Plant Patent
Egger

(10) Patent No.: US PP31,398 P2
(45) Date of Patent: Jan. 21, 2020

(54) ***PHYGELIUS* PLANT NAMED 'TNPHYCRO'**

(50) Latin Name: ***Phygelius* x *rectus***
Varietal Denomination: TNPHYCRO

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,832

(22) Filed: Jan. 18, 2019

(51) Int. Cl.
*A01H 5/02* (2018.01)
*A01H 6/00* (2018.01)

(52) U.S. Cl.
USPC ..... Plt./468
CPC ..... *A01H 6/00* (2018.05)

(58) Field of Classification Search
USPC ..... Plt./468
CPC ..... A01H 5/02
See application file for complete search history.

(56) References Cited

PUBLICATIONS https://issuu.com/monrovia4/docs/monrovia_tool_ kit_aug_20_ final; Aug. 30, 2018; 4 pages.*

* cited by examiner

*Primary Examiner* — Kent L Bell
(74) *Attorney, Agent, or Firm* — Klarquist Sparkman, LLP

(57) ABSTRACT

A new and distinct cultivar of *Phygelius* plant characterized by purple-rose flowers, a long bloom time, an upright, well branched habit, with multiple crowns from the base, clean-looking, deep green foliage, and excellent vigor.

1 Drawing Sheet

Botanical denomination: *Phygelius* x *rectus.*
Variety designation: 'TNPHYCRO'.
Trade Designation: COLORBURST™ Rose.

BACKGROUND OF THE INVENTION

The present invention relates to a new and distinct cultivar of *Phygelius*, given the name, 'TNPHYCRO'. *Phygelius* is in the family Scrophulariaceae. *Phygelius* x *rectus* 'TNPHYCRO' is from a controlled cross using *Phygelius* '86-2', a proprietary, unnamed plant as the seed parent, and *Phygelius* '89-2', a proprietary, unnamed plant as the pollen parent. It was part of a controlled breeding program to produce upright, compact habits with high flower count. This cultivar was selected for the medium size flowers, intense purple-rose flower color, upright and well branched habit, multiple crowns from the base, extended bloom time, and clean-looking, deep green foliage.

Compared to the seed parent, *Phygelius* '86-2', the new cultivar has a more intense purple-rose flower color rather than dark pink and a higher flower count.

Compared to the pollen parent, *Phygelius* '89-2', the new cultivar has a higher flower count.

Compared to *Phygelius* x *rectus* CROFTWAY™ Purple Prince 'Cropurpri' (Plant Pat. No. 18,540), the new cultivar is shorter.

Compared to *Phygelius* x *rectus, Phygelius* 'Magenta', an unpatented cultivar, the new cultivar has more pinkish-purple flowers rather than purple.

*Phygelius* 'TNPHYCRO' is uniquely distinguished by its:

1. medium size, intense purple-rose flowers,
2. high flower count,
3. long bloom time, 4. upright, well branched habit, with multiple crowns from the base,
5. clean-looking, deep green foliage, and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
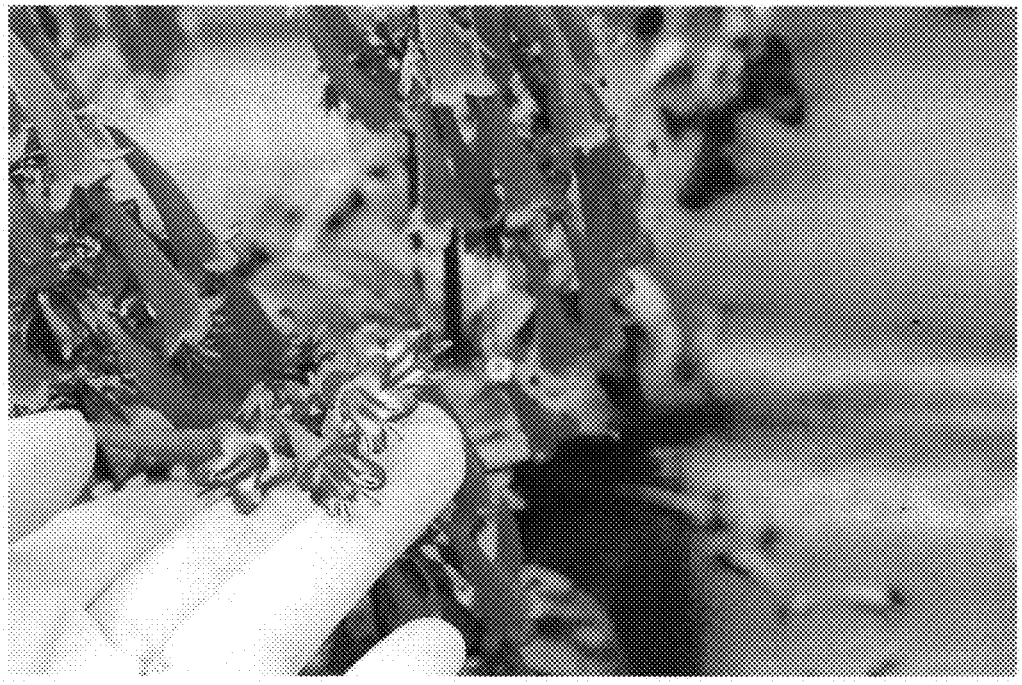
FIG. 1 shows a close up of a one-year-old *Phygelius* 'TNPHYCRO' in June in Canby, Oreg.
Figure 2:
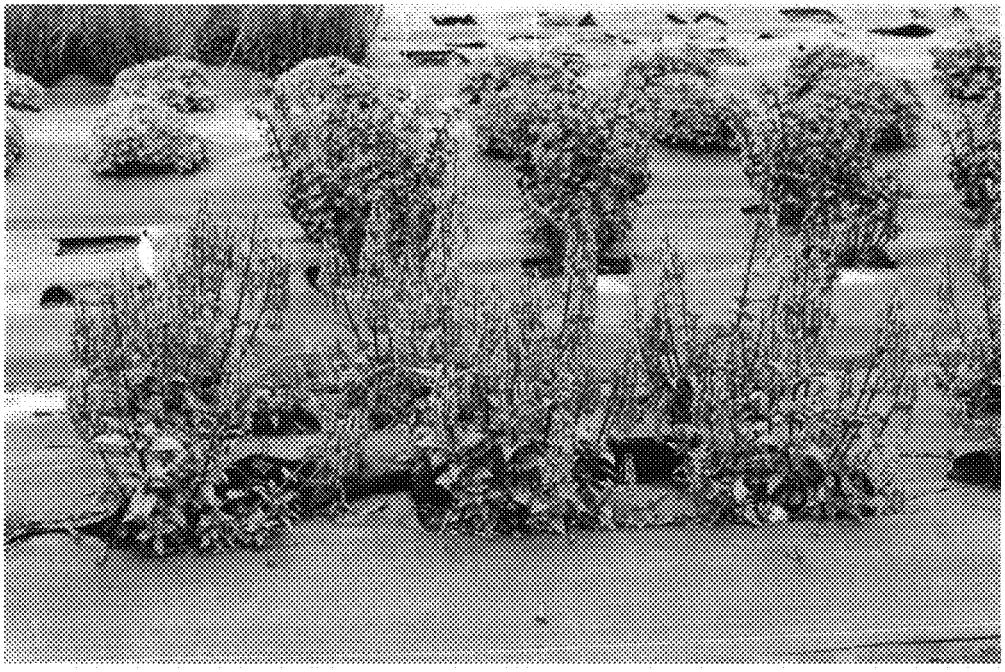
FIG. 2, foreground, shows a one-year-old *Phygelius* 'TNPHYCRO' in bloom growing in full sun in the garden in June in Canby, Oreg.

The following is a detailed description of the new *Phygelius* cultivar based on observations of an 18-month-old specimen grown outside in a one gallon pot in Canby, Oreg. in mid-June. The color descriptions are all based on The Royal Horticultural Society Colour Chart, 5$^{th}$ edition, 2007, except where general color terms of ordinary dictionary significance are used.

Plant:

*Type.*—Semi-evergreen subshrub.

*Form.*—Upright, branching.

*Cold hardiness.*—USDA Zone 7-10.

*Size.*—Grows to 95 cm tall and 96 cm wide.

*Vigor.*—Excellent.

*Stem number.*—6 main stems from the crown.

*Stem.*—Upright, grows to 38 cm long and 9 cm wide (at the base), glabrous, internodes grow to 3.8 cm long, Grey Brown 199A on older stems, younger stems Greyed Purple 187A.

*Rooting.*—Plants root easily from stem cuttings.

Leaf:

*Type.*—Simple.

*Arrangement.*—Opposite.

*Shape.*—Ovate to ovate lanceolate.

*Venation.*—Pinnate.

*Margins.*—Serrate.

*Apex.*—Acute.

*Base.*—Cuneate.

*Blade size.*—Grows to 6.2 cm long and 5.1 cm wide.

*Petiole.*—Grows to 2.9 cm long and 0.3 cm wide, closest to Greyed Orange 177A.

*Surface texture.*—Glabrous on both sides.

*Leaf color.*—Topside closest to Green N134A with main vein at base Greyed Orange 166A, bottom side Green 138B.

Inflorescence:

*Type.*—One-sided, pyramidal panicle with pendulous flowers.

*Number of flowers per inflorescence.*—About 70.

*Size of inflorescence.*—Grows to 22.5 cm long and 6 cm wide.

*Peduncle.*—Grows to 1.8 cm long and 2 mm wide, glabrous, Green 138B heavily speckled with Greyed Purple 187A.

*Pedicel.*—Grows to 1 cm long and 1 mm wide, glabrous, Greyed Purple 187A.

*Bloom period.*—June to frost in Canby, Oreg.

Flower bud:

*Size.*—3.2 cm long and 0.7 cm wide at the widest area.

*Description.*—Tubular, pendulous.

*Color.*—Closest to Red Purple 59C on top ⅓ blending to Red Purple 59C tinted with Red Purple 60D.

Flower:

*Type.*—Zygomorphic, perfect.

*Shape.*—Tubular.

*Size.*—Grows to 4.7 cm long and 1.8 cm wide.

*Corolla description.*—Grows to 4.3 cm long and 1.8 cm wide; both sides glabrous; tube 3.5 cm long, swollen to 6 cm wide on bottom side for 0.4 cm under the calyx then narrows to 0.5 cm wide and expanding to 0.9 cm wide below the lobes; 5 lobes, reflexed, oblong, tips obtuse, margins entire, lobes 7 mm long and 6 mm wide; outside color between Red Purple 71A and Red Purple 71B, inside color White 155A on the first 0.8 cm of the lobes blending to between White N155 D and White NN155C for 3 cm.

*Calyx description.*—0.8 cm deep and 0.8 cm wide, 5 spreading, slightly reflexed lobes cut almost to the base, glabrous inside and out, each lobe lanceolate in shape, 6 mm long and to 2 mm wide, margins entire, tip acute, Greyed Purple N186C.

*Pistil description.*—1, 4.8 cm long, ovary 0.6 cm long and 0.3 cm wide, Yellow Green 144D tinted Red Purple 58A; style 4.2 cm long and less than 1 mm wide, Red Purple 58A; stigma 1 mm Greyed Purple 187A.

*Stamen description.*—4, filaments: two short 1.3 cm long and two long 1.5 cm and 1 mm wide, Red Purple 58A, anthers 0.3 cm long and 0.2 cm wide, Greyed Brown N199A, pollen Greyed Brown N199A.

*Fragrance.*—None.

*Lastingness.*—A flower lasts about a week on a plant.

Fruit:

*Type.*—Capsule, curved.

*Fertility.*—Poor.

*Size.*—1 cm deep and 5 mm wide.

*Color.*—Brown 200D.

Seed: None seen.

Pests and diseases: Plants of the new *Phygelius* have not been observed to be resistant to pathogens and pests common to *Phygelius*.

I claim:

1. A new and distinct cultivar of *Phygelius* plant substantially as shown and described.

* * * * *